United States Patent
Petrov et al.

(10) Patent No.: US 6,891,041 B2
(45) Date of Patent: May 10, 2005

(54) METHOD FOR PRODUCING 4-(HETEROARYL-METHYL)-HALOGEN-1(2H)-PHTHALAZINONES

(76) Inventors: Orlin Petrov, Friedrichshaller Strasse 7B, Berlin (DE), D-14199; Thomas Heiner, Alte Jakobstrasse 78a, Berlin (DE), D-10179; Herribert Neh, Joachim-Friedrick-Strasse 18, Berlin (DE), D-10711; Martin Kruger, Heerruferweg 7a, Berlin (DE), D-13465

(*) Notice: Subject to any disclaimer, the term of this patent is extended or adjusted under 35 U.S.C. 154(b) by 0 days.

(21) Appl. No.: 10/168,794
(22) PCT Filed: Dec. 20, 2000
(86) PCT No.: PCT/EP00/13027
  § 371 (c)(1),
  (2), (4) Date: Jun. 11, 2003
(87) PCT Pub. No.: WO01/47912
  PCT Pub. Date: Jul. 5, 2001

(65) Prior Publication Data
  US 2004/0192695 A1 Sep. 30, 2004

(30) Foreign Application Priority Data
  Dec. 23, 1999 (DE) .......................... 199 63 607

(51) Int. Cl.$^7$ ...................... C07D 401/06; C07D 403/06
(52) U.S. Cl. ...................................... 544/237
(58) Field of Search ........................ 544/237

(56) References Cited

U.S. PATENT DOCUMENTS

| 4,251,528 A | * | 2/1981 | Brittain et al. | ............ 514/232.8 |
| 5,849,741 A | * | 12/1998 | Watanabe et al. | ............ 514/248 |
| 6,114,530 A | * | 9/2000 | Yuan et al. | .................. 546/143 |
| 6,340,684 B1 | * | 1/2002 | Napoletano et al. | ......... 514/248 |
| 6,706,882 B2 | * | 3/2004 | Napoletano | .............. 546/284.1 |

FOREIGN PATENT DOCUMENTS

| EP | 634404 | * | 1/1995 |
| WO | 98/35958 | * | 8/1998 |
| WO | 99/32456 | * | 7/1999 |
| WO | 00/05218 | * | 2/2000 |

OTHER PUBLICATIONS

Napoletano et al. Bioorganic & Medicinal Chemistry Letters vol. 11, p. 33–37 (2001).*

* cited by examiner

*Primary Examiner*—Emily Bernhardt
(74) *Attorney, Agent, or Firm*—Millen, White, Zelano & Branigan, P.C.

(57) ABSTRACT

A process for the production of 4-(heteroaryl-methyl)-halogen-1(2H)-phthalazinones, especially 4-(4-pyridylmethyl)-1(2H)-phthalazinone, is described, which is characterized by the reaction of phthalidyl-3-triphenylphosphonium salt with 4-pyridine aldehyde in the presence of a basic adjuvant, subsequent reaction with hydrazine hydrate and subsequent acid treatment, whereby this process avoids the technical safety and environmental problems of the known processes.

9 Claims, No Drawings

METHOD FOR PRODUCING 4-(HETEROARYL-METHYL)-HALOGEN-1(2H)-PHTHALAZINONES

The invention relates to a process for the production of 4-(heteroaryl-methyl)-halogen-1(2H)-phthalazinones.

4-(Heteroaryl-methyl)-halogen-1(2H)-phthalazinone, especially the 4-(4-pyridylmethyl)-1(2H)-phthalazinone, are valuable intermediate products in the production of phthalazine derivatives, which are distinguished by pharmacologically advantageous properties, such as, e.g., inhibition of angiogenesis (WO 98/35958), inhibition of cGMP phosphodiesterase (EP 0 722 936), inflammation-inhibiting and antihypertensive action (DE OS 2 021 195) and thus open up new therapeutic possibilities, especially for treating cancer and heart disease.

The production of, for example, 4-(4-pyridylmethyl)-1 (2H)-phthalazinone is carried out according to previously known methods by the reaction of phthalic acid anhydride and 4-methylpyridine at about 200° C. and subsequent reaction of the condensation product that is obtained (γ-pyrophthalone) with excess hydrazine at 130° C. (DE AS 1 061 788). Drawbacks of these methods are the low yield (<50%), low product quality and primarily the necessarily very high temperature of the condensation reaction, which makes very difficult an industrial-scale application of the methods.

As an alternative, 4-(4-pyridylmethyl)-1(2H)-phthalazinone can be produced by condensation of phthalide with 4-pyridine aldehyde in the presence of sodium methylate and subsequent reaction of the 2-(4(1H)-pyridinylidene)-4,5,6,7-tetrahydroindene-1,3-dione that is obtained with a large excess (16 equivalents) of hydrazine at 130° C. (WO 98/35958). The yield over the two stages is about 40% of theory. In the case of these methods, the handling of the large excess of carcinogenic hydrazine at a temperature that lies above the decomposition temperature of hydrazine (about 120° C.) is very problematical in nature. In this case, it is very unlikely that the very low boundary value for hydrazine in air (MAK 0.008 ppm) or in waste waters can be maintained in the working-up and isolation of the product.

From WO 99/32456, a reaction is known that is performed, however, with about 100× excess of hydrazine and at a reaction temperature that is close to the decomposition temperature of hydrazine (about 120° C.). On an industrial scale, such a process is very problematical in nature. The yield is also comparatively low.

It would therefore be desirable to have a viable process for the production of 4-(heteroaryl-methyl)-halogen-1(2H)-phthalazinones, especially 4-(4-pyridylmethyl)-1(2H)-phthalazones, which avoids the technical problems (reaction at 200° C.), safety problems (heating of hydrazine to 130° C.) and environmental problems (large excess of hydrazine) of the known processes.

The known drawbacks are now overcome by the process according to the invention.

The subject of the invention is thus a process for the production of 4-(heteroaryl-methyl)-halogen-1(2H)-phthalazinones of general formula I

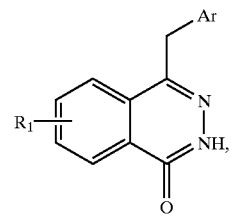

in which $R^1$=fluorine, chlorine, bromine or hydrogen and Ar=pyridine, pyrazine or pyrimidine, characterized in that substituted phthalidyl-3-triphenylphosphonium salts of general formula II

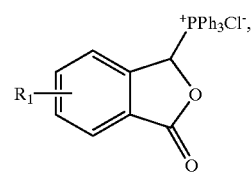

in which $R^1$=fluorine, chlorine, bromine or hydrogen, are reacted with aldehydes of general formula III

Ar—CHO    III, in which Ar=pyridine, pyrazine or pyrimidine, in the presence of a base and subsequent reaction with hydrazine hydrate and optionally under acidic conditions.

Radical $R^1$, if the latter should stand for halogen, can be in any position on the phenyl ring within the pyrazinone system, thus in 1-, 2-, 3- or 4-position. As suitable Ar radicals, pyridine, pyrimidine or pyrazine can be mentioned. Suitable aldehydes are, for example, 2-, 3- or 4-pyridine-aldehyde, 2-methyl-4-pyridine-aldehyde, 3-methyl-4-pyridine-aldehyde, 4-pyrimidine-aldehyde, 5-pyrimidine-aldehyde, 3-pyrazine-aldehyde or 4-pyrazine-aldehyde.

Thus, for example by the reaction of phthalidyl-3-triphenylphosphonium salt with 4-pyridine aldehyde in the presence of a base (basic adjuvant), subsequent reaction with hydrazine hydrate and acid treatment of the reaction mixture. In particular, subsequent reaction with 1–1.1 equivalents of hydrazine hydrate and subsequent treatment of the reaction mixture with 0.1–0.3 equivalent of acetic acid anhydride triggered by the reaction in a solvent of phthalidyl-3-triphenylphosphonium salts with 4-pyridine aldehyde in the presence of a base (basic adjuvant).

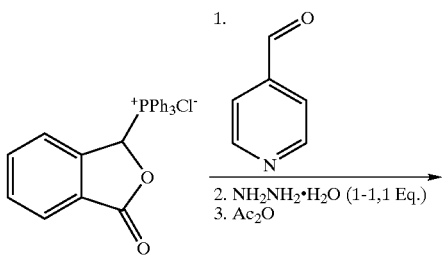

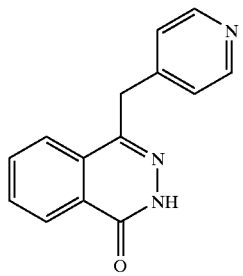

To isolate the product, the reaction mixture is mixed with an aqueous acid, the solvent is distilled off, the precipitated triphenylphosphine is filtered off, and the filtrate is alkalized. The desired product is precipitated in this case and is obtained at a very high purity and excellent yield (95–98% of theory) after filtration and drying.

As a solvent for the reaction, organic solvents, such as, for example, tetrahydrofuran, dimethoxyethane, methanol, ethanol or dimethylformamide, are suitable. As bases, organic bases, such as amines, e.g., triethylamine, ethyldiisopropylamine, or inorganic bases such as potassium carbonate, sodium carbonate, magnesium carbonate or magnesium hydroxides are used. The reaction time for the reaction of phthalidyl-3-triphenylphosphonium salts is 1 hour at 40° C. and for the reaction with hydrazine is 7–14 hours at 50–70° C.

The phthalidyl-3-triphenylphosphonium salts (bromides and chlorides) that are used as educts are easily accessible according to methods that are known in the literature (J. Organometallic Chem. 1972, 391; J. Org. Chem. 1973, 4164).

Advantages of the process according to the invention compared to the processes that are known from the prior art are the less severe reaction conditions, significantly better yield (>90%) and especially the use of stoichiometric amounts of hydrazine. The reactions proceed fully and in a closed system, so that before the working-up, no hydrazine can be detected in the reaction mixture (single-pot reaction). The threat posed by this carcinogen is thus avoided.

Embodiments

EXAMPLE 1

Production of 4-(4-Pyridylmethyl)-phthalazinone 500 g of phthalidyl-3-triphenylphosphonium chloride (1.160 mol) is suspended in 2250 ml of tetrahydrofaran (THF). At 5° C., 110.7 ml of pyridine-4-aldehyde (124.2 g, 1.160 mol) is added, and then 161.7 ml of triethylamine (117.4 g, 1.160 mol) is metered into the white suspension. After the addition is completed, the reaction mixture is stirred for 1 hour at 40° C., then mixed with 62.0 ml of hydrazine hydrate (63.9 g, 1.276 mol) and stirred for 8 hours at 70° C. Then, 32.7 ml of acetic acid anhydride (35.5 g, 0.348 mol) is added, and the stirring is continued for 2.5 hours at 20° C. Then, the reaction mixture is mixed first with 1500 ml of water, then with 367 ml of 4 M $H_2SO_4$ solution. About 2500 ml of THF/water is distilled off from this reaction solution in a vacuum. The suspension that is obtained is filtered via a glass frit. The filtrate is mixed with 50% sodium hydroxide solution up to a pH of 8.0 (about 185 ml). The precipitated product is filtered off, washed with 450 ml of water and dried at 60° C. 264.2 g (96% of theory) of a slightly yellowish solid is obtained.

Melting point: 193–194° C. EI-MS (M+H) 242.

The production of the other derivatives is carried out analogously to this example.

What is claimed is:

1. A process for preparing (heteroaryl-methyl)-halogen-1 (2H)-phthalazinones of formula I

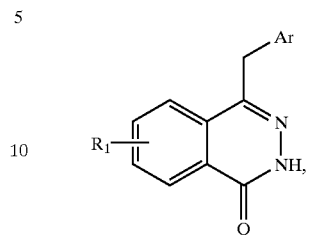

in which
$R^1$=fluorine, chlorine, bromine or hydrogen and
Ar=pyridine, pyrazine or pyrimidine,
comprising reacting a substituted phthalidyl-3-triphenylphosphonium salt of formula II

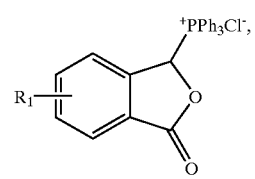

in which
$R^1$=fluorine, chlorine, bromine or hydrogen,
with an aldehyde of formula III Ar—CHO      III, in which
Ar=pyridine, pyrazine or pyrimidine,
in the presence of a base, and
subsequent reaction with hydrazine hydrate and optionally under acidic conditions.

2. A process according to claim 1, wherein the base is an amine, an alkali hydroxide or an alkaline-earth hydroxide.

3. A process according to claim 1, wherein the reaction with hydrazine hydrate and subsequent treatment of the reaction mixture is carried out with acetic acid anhydride or acetic acid.

4. A process according to claim 1, wherein the reaction with hydrazine hydrate is carried out with 1–1.1 equivalents of hydrazine hydrate.

5. A process according to claim 1, wherein the treatment of the reaction mixture is carried out with 0.1–0.3 equivalent of acetic acid anhydride.

6. A process according to claim 1, wherein the reaction of a compound of formula I and of formula II takes place for about 1 hour at about 40° C.

7. A process according to claim 1, wherein the reaction of hydrazine with the reaction mixture takes place for 7–14 hours at 50–70° C.

8. A process according to claim 1, wherein the process of claim 1 is performed as a single-pot process.

9. A process according to claim 1, wherein the reaction mixture after reaction with hydrazine hydrate essentially does not contain hydrazine hydrate.

* * * * *